United States Patent

Szymczakowski et al.

[11] Patent Number: 5,832,959
[45] Date of Patent: Nov. 10, 1998

[54] STOPCOCKS

[75] Inventors: Tadeusz A. Szymczakowski, Odakra; Ulf H. Wahlberg, Helsingborg, both of Sweden

[73] Assignee: Becton Dickinson Infusion Therapy AB, Helsingborg, Sweden

[21] Appl. No.: 726,250

[22] Filed: Oct. 4, 1996

[30] Foreign Application Priority Data

Oct. 16, 1995 [GB] United Kingdom .................... 9521120

[51] Int. Cl.⁶ ............................. F16K 11/085; F16K 5/04; F16K 37/00
[52] U.S. Cl. ..................... 137/625.47; 137/556; 251/297; 251/309; 251/904
[58] Field of Search ............................... 137/556, 625.47; 251/297, 309, 904

[56] References Cited

U.S. PATENT DOCUMENTS

| 3,012,752 | 12/1961 | Buck | 251/904 X |
|---|---|---|---|
| 3,344,785 | 10/1967 | Hamilton | 137/624.47 X |
| 3,481,367 | 12/1969 | Deuschle | 251/309 X |
| 3,678,960 | 7/1972 | Leibinsohn | 251/904 X |
| 3,750,704 | 8/1973 | Burke et al. | 137/625.47 |
| 3,774,604 | 11/1973 | Danielsson | 251/904 X |
| 3,783,900 | 1/1974 | Waldbillig | 251/309 X |
| 3,788,599 | 1/1974 | Cloyd | 251/904 X |
| 4,073,314 | 2/1978 | Speelman et al. | 137/625.47 |
| 4,207,923 | 6/1980 | Giurtino | 137/625.47 |
| 4,314,586 | 2/1982 | Folkman | 251/904 X |
| 4,593,717 | 6/1986 | Levasseur | 137/625.47 X |
| 4,807,666 | 2/1989 | Morse | 251/904 X |
| 4,890,817 | 1/1990 | Uri | 251/904 X |
| 5,183,077 | 2/1993 | Keiper | 137/625.47 |

FOREIGN PATENT DOCUMENTS

| UM 4-29619 | 7/1992 | Japan . |
|---|---|---|
| 648751 | 10/1945 | United Kingdom . |
| 682095 | 2/1950 | United Kingdom . |
| 91/96331 | 5/1991 | WIPO . |

*Primary Examiner*—John Rivell
*Attorney, Agent, or Firm*—Eric M. Lee; Roger M. Rathbun

[57] ABSTRACT

A stopcock comprises a hollow barrel which receives in a rotatable manner a co-operating tap. A section of the tap is formed with holes which allow communication between selected hollow spigots extending from the barrel. A further section of the tap of larger diameter than the section is formed with indents which engage with detents formed on a large diameter section of the barrel to provide a positive indication when the tap is rotated within the hollow barrel to one or more selected positions.

3 Claims, 4 Drawing Sheets

STOPCOCKS

BACKGROUND OF THE INVENTION

The present invention relates to stopcocks and in particular to stopcocks used in medical applications.

Medical stopcocks are known and used for controlling and directing the flow of a medical liquid along a selected path. In the administration of liquids such as blood, saline or other medical liquids to a patient undergoing medical treatment, it is frequently necessary to direct the flow of the medical liquid from a first conduit or tube to a further conduit or tube selected from a possible two or more conduits or tubes. This is usually accomplished by using a stopcock.

Stopcocks are known which comprise a barrel member which receives in a rotatable manner a co-operating tap. Usually there extends from the barrel two or more hollow spigots to which can be attached tubes for the flow therethrough of the medical liquid. The body of the tap is formed with holes which, depending on the rotational position of the tap relative to the barrel will permit the flow of medical liquid from one inlet tube to a selected one of the remaining outlet tubes.

Usually, the holes in the body of the tap are so arranged that in at least one rotational position of the tap relative to the barrel, all flow of medical liquid from said one inlet tube to an outlet tube is prevented.

In these known stopcocks it is sometimes difficult for the user to ascertain with certainty when the tap is in the correct angular position relative to the barrel to allow full flow of the medical liquid from the one inlet tube to the selected outlet tube. If the appropriate hole in the tap is not fully aligned with the corresponding spigot, then the flow of the medical liquid can be impeded. Likewise, in the non-flow position of the stopcock, if the holes in the body of the tap are not completely out of alignment with the spigots then the medical liquid might seep into one of the outlet spigots.

Japanese utility model Publication No 4-29619 describes a stopcock which comprises a hollow barrel from which extends a plurality of spaced, hollow spigots the interiors of which communicate with the interior of the hollow barrel; and a tap having a body part mounted for rotational movement within the hollow barrel and having a plurality of holes for allowing communication between selected spigots. The body part is a liquid tight fit within the hollow barrel but includes a reduced diameter portion formed with a plurality of indents. The corresponding portion of the hollow barrel is formed with projections such that when the tap is rotated relative to the hollow barrel a positive indication or click is given for all the positions which allow the flow of medical liquid through the stopcock.

The formation of the indents on a reduced diameter portion of the body part sometimes makes it difficult to sense when the tap has reached a selected position. This is particularly so after considerable use of the stopcock.

It is an aim of the present invention to obviate this disadvantage by providing co-operating indents and detents on larger diameter sections of the barrel and tap which will give a positive indication throughout the working life of the stopcock as to when the inlet spigot is aligned with a selected outlet spigot or when the stopcock is in its closed position.

It is a further aim of the present invention to provide a stopcock for medical applications which is relatively simple to manufacture and assemble and therefore economical to produce.

BRIEF SUMMARY OF THE INVENTION

According to the present invention, a stopcock for medical purposes comprises a hollow barrel from which extends a plurality of spaced, hollow spigots the interiors of which communicate with the interior of the hollow barrel; and a tap having a body part mounted for rotational movement within the hollow barrel and having a plurality of holes for allowing communication between selected spigots, the body part within the hollow barrel being a liquid tight fit within said hollow barrel, and means provided on the barrel and the tap which co-operate to give a positive indication when the body part of the tap is rotated within the hollow barrel to one or more selected positions, characterised in that the hollow barrel has a relatively small internal diameter section which receives a corresponding section of the body part of the tap in a liquid tight manner and a further section of larger internal diameter on which are formed one or more detents; and the body part of the tap has a corresponding section of larger diameter than the section which is received within the relatively small interior diameter of the barrel on which are formed a plurality of indents.

Preferably, the tap is provided with a further section on which is formed a resilient rib for latching the body part of the tap to the hollow barrel.

In a preferred embodiment the resilient rib extends no more than 180 degrees around the further section.

BRIEF SUMMARY OF THE DRAWINGS

An embodiment of the invention will now be described, by way of example, reference being made to the FIGS. of the accompanying diagrammatic drawings in which.

DETAILED DESCRIPTION OF THE PREFERRED EMBODIMENTS

Figure 1:
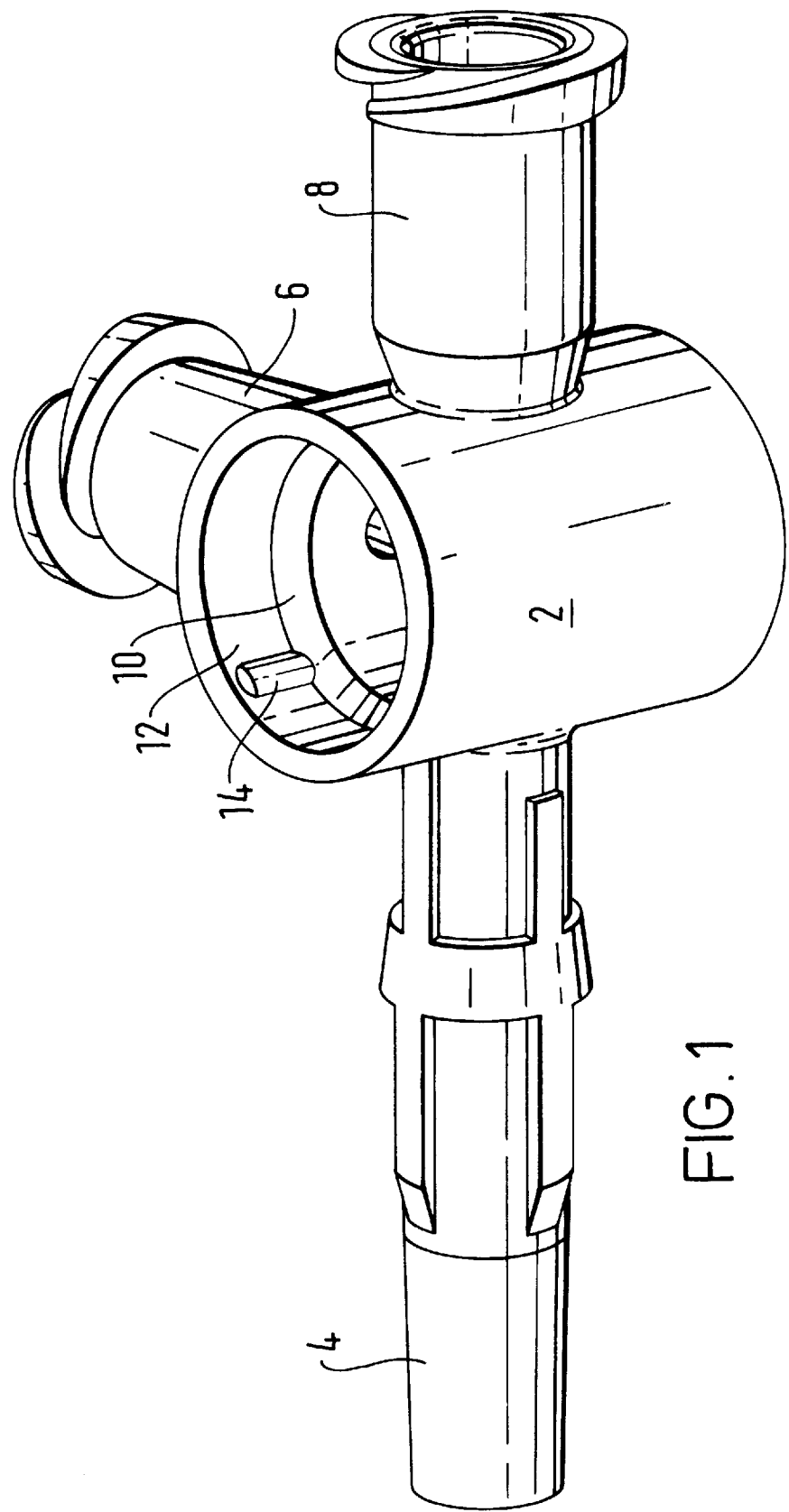
FIG. 1 is a perspective view of a barrel forming part of a stopcock according to the present invention.
Figure 2:
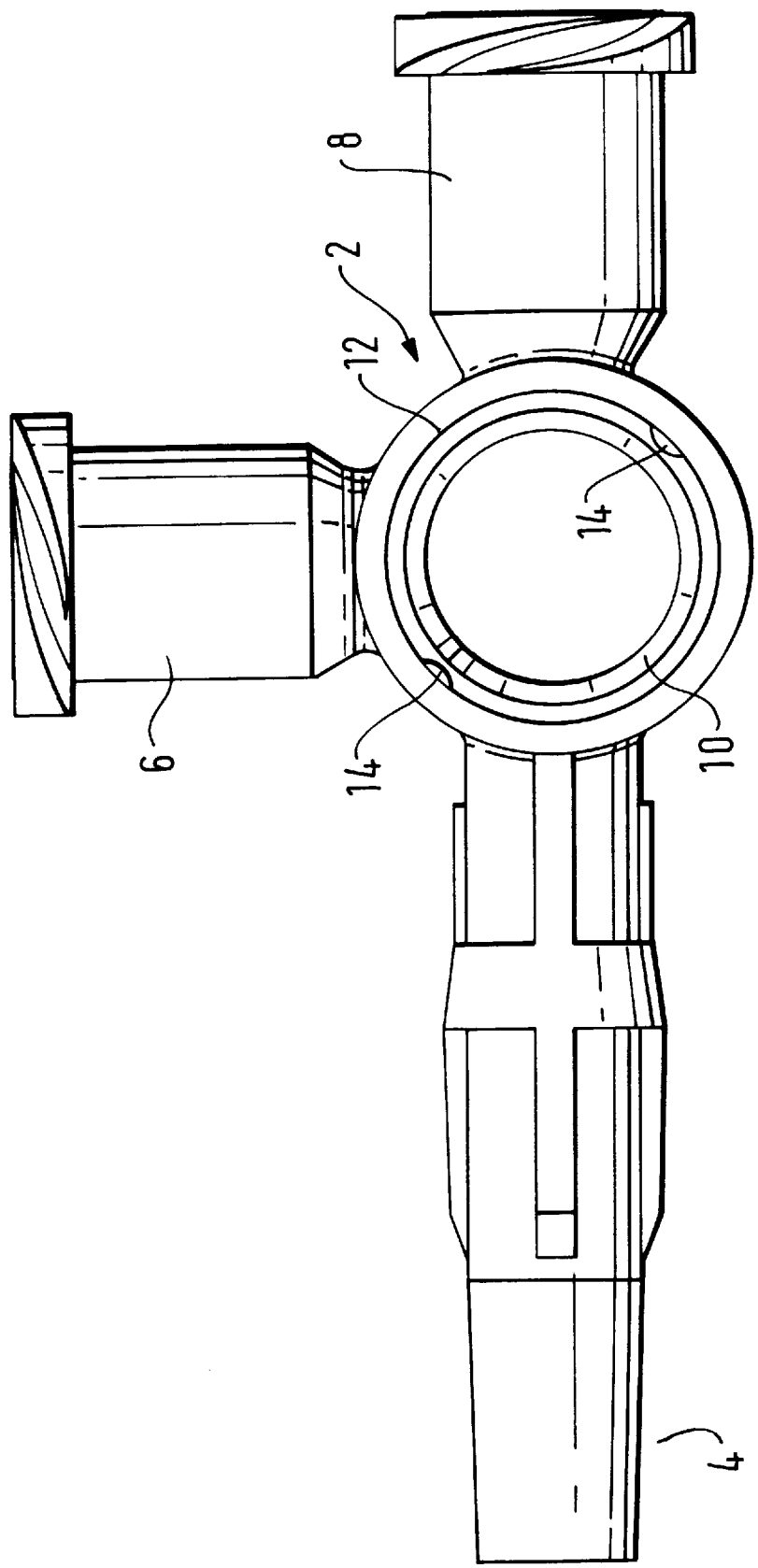
FIG. 2 is a plan view of the barrel of FIG. 1.

Referring first to FIGS. 1 and 2, a barrel 2 forming part of a stopcock has a hollow interior. Extending radially outwardly from the outward facing surface of the barrel 2 are three spaced hollow spigots 4, 6, 8. Each spigot is adapted in a manner known per se to be connected to a tube (not shown). As is known, at least one of the inlets, that is, spigot 8 or 6 will be connected to a tube through which medical liquid will flow from a source. The remaining outlet spigot 4 will be connected to a tube which, as will be explained, will conduct the medical liquid from the stopcock towards a patient or other destination.

The hollow spigots 4, 6, 8 each communicate with the interior of the barrel 2 at a main, relatively small diameter interior section 10. A larger diameter interior section 12 extends from the section 10 upwardly (as shown in FIG. 1) and on the surface of the larger diameter section 12 are formed two detents 14.

Figure 3:
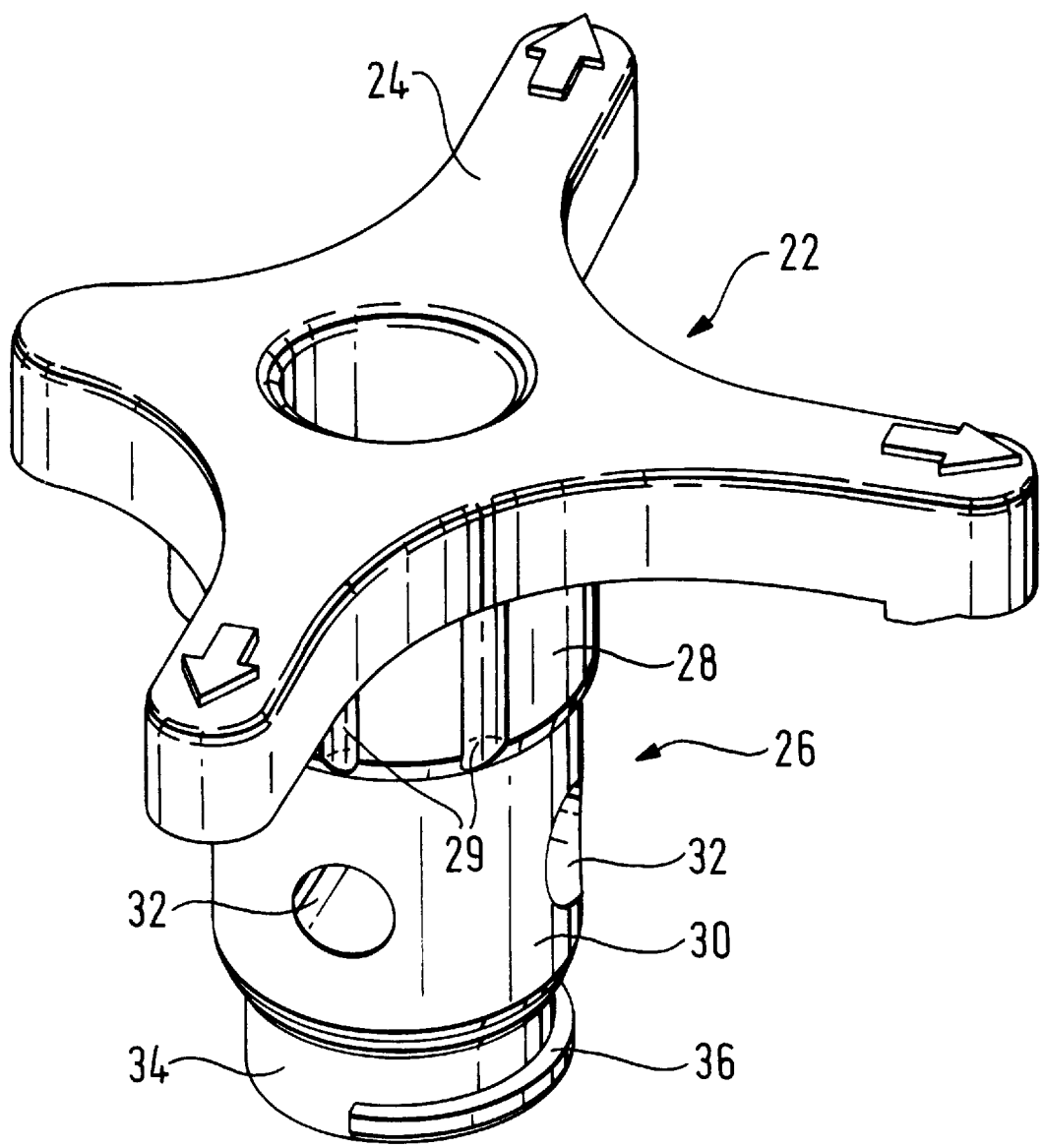
FIG. 3 is a perspective view of a tap forming part of a stopcock according to the present invention.
Figure 4:
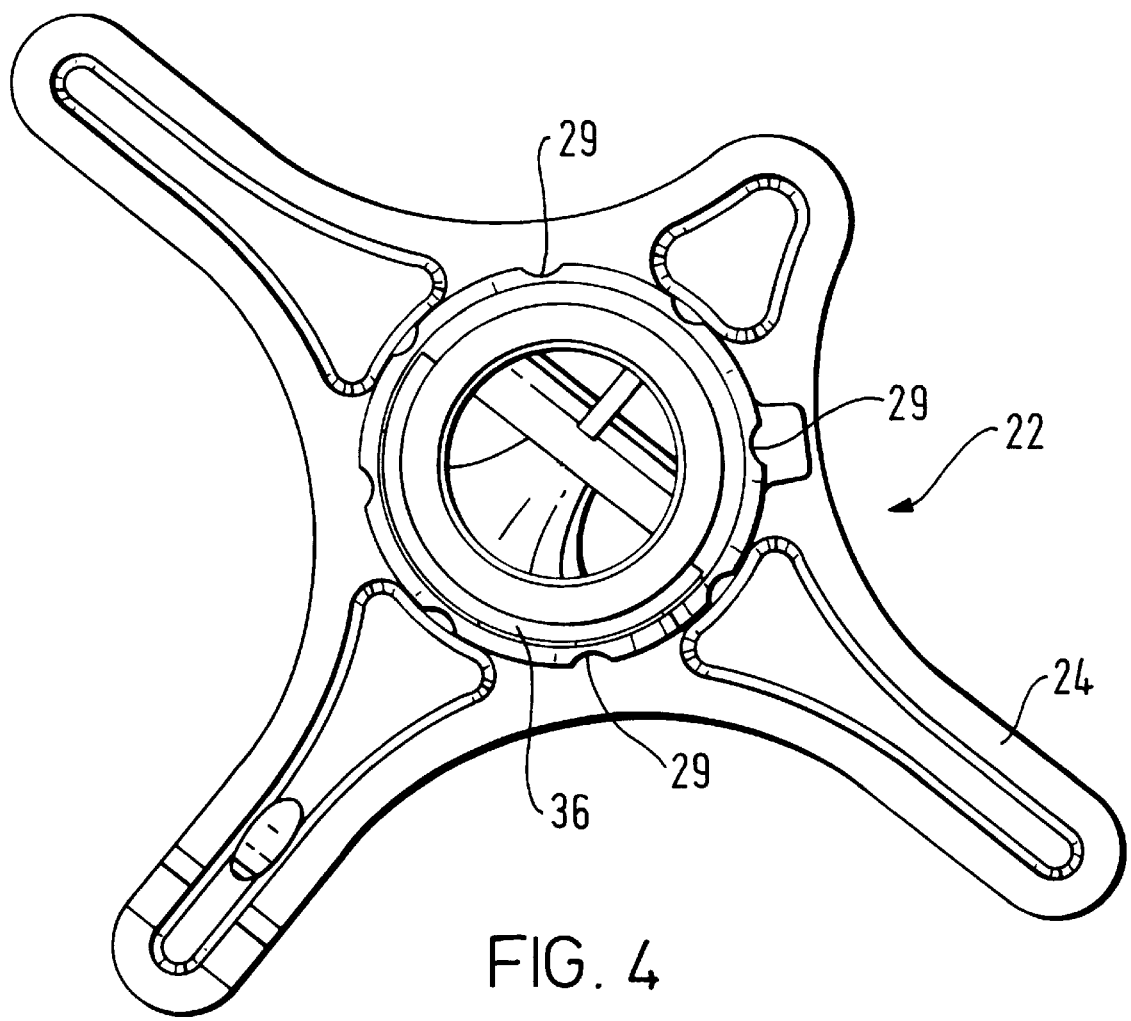
FIG. 4 is a reverse plan view of the tap of FIG. 3.
Figure 5:
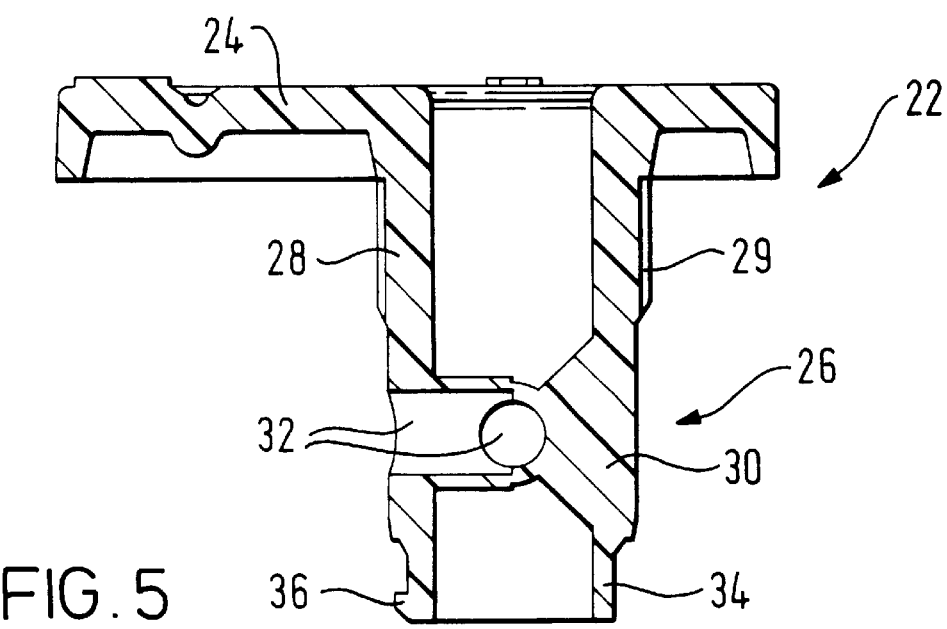
FIG. 5 is a cross-section through the tap of FIGS. 3 and 4.

Referring now to FIGS. 3, 4 and 5, a tap 22 for co-operating with the barrel 2 comprises a handle 24 from which depends a body part 26. The body part 26 includes a first section 28 immediately adjacent the handle 24 of relatively large diameter. Formed on the section 28 are a plurality namely eight as shown, indents 29.

Below (as shown in FIGS. 3 and 5) and immediately adjacent the section 28 is a middle section 30 of small diameter than the section 28. Formed in the middle section 30 are holes 32. The diameter of the middle section 30 is so dimensioned relative to the section 10, that the tap 22 can be rotated when mounted within the barrel 2 but at the same time, the sections 10, 30 are a liquid tight fit.

Finally, adjacent the section 30 is a section 34 of smaller diameter than the middle section 30. Formed on the outer surface of the section 34 is a resilient rib 36 which extends substantially but no more than 180 degrees around the outer surface of the section 34. The resilient rib 36 has also a smaller diameter than section 10 and the rounded corner between sections 30 and 34 is applied to simplify the assembly.

Both the barrel 2 and the tap 22 are made from resilient plastics material eg. polyethylene for the tap and polycarbonate for the barrel and both can conveniently be made by plastics moulding techniques.

On assembly, the tap 22 is forced through the upper (as shown) end of the barrel 2 until the rib 36 snaps resiliently adjacent the lower end of the barrel 2. This will automatically ensure that the tap 22 is retained within the barrel 2 and that the holes 32 can be aligned with the hollow spigots 4, 6, 8.

In use, when it is desired, for example, to direct medical liquid flowing into the inlet spigot 8 towards the outlet spigot 4 then the handle of the tap is turned until the holes 32 in the middle section 30 of the tap 22 are aligned with the appropriate spigots 8, 4. The operator knows when the alignment is achieved since he will feel the appropriate indents 29 and detents 14 engaging. Thus, the operator will be in no doubt at all that the full flow of medical liquid is unimpeded during its journey through the stopcock.

Likewise, when it is desired to stop the flow of fluid the handle 24 can be moved and again the operator will feel the engagement of the appropriate indents and detents. Since the sections 10, 30 provide a liquid tight seal then no liquid from the inlet spigot 8 will pass through the stopcock.

We claim:

1. A stopcock comprising a hollow barrel from which extends a plurality of spaced, hollow spigots the interiors of which communicate with the interior of the hollow barrel; and a tap having a body part mounted for rotational movement within the hollow barrel and having a plurality of holes for allowing communication between selected spigots, the body part within the hollow barrel being a liquid tight fit within said hollow barrel, and means provided on the barrel and the tap which co-operate to give a positive indication when the body part of the tap is rotated within the hollow barrel to one or more selected positions, in which the hollow barrel has a relatively small internal diameter section which receives a corresponding section of the body part of the tap in a liquid tight manner and a further section of larger internal diameter on which are formed one or more detents; and the body part of the tap having a corresponding section of larger diameter than the section which is received within the relatively small interior diameter of the barrel on which are formed a plurality of indents.

2. A stopcock as claimed in claim 1, in which the tap is provided with a further section on which is formed a resilient rib for latching the body part of the tap to the hollow barrel.

3. A stopcock as claimed in claim 2, in which the resilient rib extends no more than 180 degrees around the further section.

\* \* \* \* \*